United States Patent
Sink

(10) Patent No.: US 7,090,670 B2
(45) Date of Patent: Aug. 15, 2006

(54) MULTI-SPOT LASER SURGICAL APPARATUS AND METHOD

(75) Inventor: Robert K Sink, Mountain View, CA (US)

(73) Assignee: Reliant Technologies, Inc., Mountain View, CA (US)

( * ) Notice: Subject to any disclaimer, the term of this patent is extended or adjusted under 35 U.S.C. 154(b) by 46 days.

(21) Appl. No.: 10/751,041

(22) Filed: Dec. 31, 2003

(65) Prior Publication Data

US 2005/0143719 A1    Jun. 30, 2005

(51) Int. Cl.
*A61B 18/18* (2006.01)
*A61B 18/20* (2006.01)
*A61N 5/01* (2006.01)
*A61N 5/067* (2006.01)

(52) U.S. Cl. .......................... 606/9; 128/898; 607/88; 607/89

(58) Field of Classification Search ................ 128/898; 606/9; 607/88–89
See application file for complete search history.

(56) References Cited

U.S. PATENT DOCUMENTS

| | | | |
|---|---|---|---|
| 3,622,743 A | 11/1971 | Muncheryan | |
| 3,721,486 A | 3/1973 | Bramley | |
| 4,653,495 A | 3/1987 | Nanaumi | |
| 4,672,969 A | 6/1987 | Dew | |
| 4,718,416 A | 1/1988 | Nanaumi et al. | |
| 4,733,660 A | 3/1988 | Itzkan | |
| 4,976,709 A | 12/1990 | Sand | |
| 5,000,752 A | 3/1991 | Hoskin et al. | |
| 5,002,051 A | 3/1991 | Dew et al. | |
| 5,192,278 A | 3/1993 | Hayes et al. | |
| 5,282,797 A | 2/1994 | Chess | |
| 5,312,396 A | 5/1994 | Feld et al. | |
| 5,330,517 A | 7/1994 | Mordon et al. | |
| 5,336,217 A | 8/1994 | Buys et al. | |
| 5,343,235 A * | 8/1994 | Fukui et al. ................ | 347/131 |
| 5,423,803 A | 6/1995 | Tankovich et al. | |
| 5,474,549 A | 12/1995 | Ortiz et al. | |
| 5,558,666 A | 9/1996 | Dewey et al. | |
| 5,595,568 A | 1/1997 | Anderson et al. | |
| 5,618,284 A | 4/1997 | Sand | |
| 5,643,252 A | 7/1997 | Waner et al. | |
| 5,707,403 A | 1/1998 | Grove et al. | |
| 5,735,844 A | 4/1998 | Anderson et al. | |
| 5,742,136 A * | 4/1998 | Ono et al. ................ | 318/135 |
| 5,746,735 A | 5/1998 | Furumoto et al. | |
| 5,759,200 A | 6/1998 | Azar | |
| 5,810,801 A | 9/1998 | Anderson et al. | |
| 5,817,089 A | 10/1998 | Tankovich et al. | |
| 5,830,208 A | 11/1998 | Muller | |
| 5,843,073 A | 12/1998 | Sinofsky | |

(Continued)

FOREIGN PATENT DOCUMENTS

WO    WO 01/26573 A1    4/2001

(Continued)

OTHER PUBLICATIONS

US 6,344,051, 2/2002, Dumoulin-White (withdrawn).

(Continued)

*Primary Examiner*—Henry M. Johnson, III
(74) *Attorney, Agent, or Firm*—Fenwick & West LLP

(57) ABSTRACT

An array of light beams is swept along a main scan direction and dithered in a sub-scan direction to generate a treatment pattern of spots. The array is elongated along the sub-scan direction and the dithering has a travel that is significantly less than the length of the array in the sub-scan direction.

36 Claims, 6 Drawing Sheets

U.S. PATENT DOCUMENTS

| | | | |
|---|---|---|---|
| 5,860,967 A | 1/1999 | Zavislan et al. | |
| 5,860,968 A | 1/1999 | Wojcik et al. | |
| 5,885,211 A | 3/1999 | Eppstein et al. | |
| 5,897,549 A | 4/1999 | Tankovich | |
| 5,925,035 A | 7/1999 | Tankovich | |
| 5,938,657 A | 8/1999 | Assa et al. | |
| 5,947,956 A | 9/1999 | Karell | |
| 5,957,915 A | 9/1999 | Trost | |
| 5,964,749 A | 10/1999 | Eckhouse et al. | |
| 5,968,033 A | 10/1999 | Fuller et al. | |
| 5,983,900 A | 11/1999 | Clement et al. | |
| 6,015,404 A | 1/2000 | Altshuler et al. | |
| RE36,634 E | 3/2000 | Ghaffari | |
| 6,036,684 A | 3/2000 | Tankovich et al. | |
| 6,050,990 A | 4/2000 | Tankovich et al. | |
| 6,059,820 A | 5/2000 | Baronov | |
| 6,063,108 A * | 5/2000 | Salansky et al. | 607/89 |
| 6,083,217 A | 7/2000 | Tankovich | |
| 6,096,029 A | 8/2000 | O'Donnell, Jr. | |
| 6,106,514 A | 8/2000 | O'Donnell, Jr. | |
| RE36,872 E | 9/2000 | Zair | |
| 6,120,497 A | 9/2000 | Anderson et al. | |
| 6,142,939 A | 11/2000 | Eppstein et al. | |
| 6,149,644 A | 11/2000 | Xie | |
| 6,152,917 A | 11/2000 | Tankovich | |
| 6,162,211 A | 12/2000 | Tankovich et al. | |
| 6,171,302 B1 | 1/2001 | Talpalriu et al. | |
| 6,197,020 B1 | 3/2001 | O'Donnell, Jr. | |
| 6,219,575 B1 | 4/2001 | Nemati | |
| 6,235,015 B1 | 5/2001 | Mead et al. | |
| 6,241,753 B1 | 6/2001 | Knowlton | |
| 6,267,771 B1 | 7/2001 | Tankovich et al. | |
| 6,273,884 B1 | 8/2001 | Altshuler et al. | |
| 6,315,772 B1 | 11/2001 | Marchitto et al. | |
| 6,328,733 B1 | 12/2001 | Trost | |
| 6,350,261 B1 | 2/2002 | Domankevitz et al. | |
| 6,375,672 B1 | 4/2002 | Aksan et al. | |
| 6,387,089 B1 | 5/2002 | Kreindel et al. | |
| 6,391,022 B1 | 5/2002 | Furumoto et al. | |
| 6,395,000 B1 | 5/2002 | Mitchell et al. | |
| 6,406,474 B1 | 6/2002 | Neuberger et al. | |
| 6,413,267 B1 | 7/2002 | Dumoulin-White et al. | |
| 6,436,127 B1 * | 8/2002 | Anderson et al. | 607/89 |
| 6,443,946 B1 | 9/2002 | Clement et al. | |
| 6,443,978 B1 | 9/2002 | Zharov | |
| 6,508,813 B1 | 1/2003 | Altshuler | |
| 6,511,475 B1 | 1/2003 | Altshuler et al. | |
| 6,514,244 B1 | 2/2003 | Pope et al. | |
| 6,514,278 B1 | 2/2003 | Hibst et al. | |
| 6,517,532 B1 | 2/2003 | Altshuler et al. | |
| 6,529,543 B1 | 3/2003 | Anderson et al. | |
| 6,533,776 B1 | 3/2003 | Asah et al. | |
| 6,537,270 B1 | 3/2003 | Elbrecht et al. | |
| 6,569,155 B1 | 5/2003 | Connors et al. | |
| 6,569,156 B1 | 5/2003 | Tankovich et al. | |
| 6,572,637 B1 | 6/2003 | Yamazaki et al. | |
| 6,575,963 B1 | 6/2003 | Van Saarloos et al. | |
| 6,579,283 B1 | 6/2003 | Tobinick | |
| 6,585,725 B1 * | 7/2003 | Mukai | 606/10 |
| 6,605,080 B1 | 8/2003 | Altshuler et al. | |
| 6,607,523 B1 | 8/2003 | Asah et al. | |
| 6,613,040 B1 | 9/2003 | Tankovich et al. | |
| 6,613,042 B1 | 9/2003 | Tankovich et al. | |
| 6,632,219 B1 | 10/2003 | Baranov et al. | |
| 6,652,512 B1 | 11/2003 | Ota | |
| 6,653,618 B1 | 11/2003 | Zenzie | |
| 6,659,999 B1 | 12/2003 | Anderson et al. | |
| 6,676,654 B1 | 1/2004 | Balle-Petersen et al. | |
| 6,695,835 B1 | 2/2004 | Furuno et al. | |
| 6,723,090 B1 | 4/2004 | Altshuler et al. | |
| 6,746,444 B1 | 6/2004 | Key | |
| 6,758,845 B1 | 7/2004 | Weckwerth et al. | |
| 6,788,967 B1 | 9/2004 | Ben-Haim et al. | |
| 6,805,428 B1 * | 10/2004 | Otsuki | 347/40 |
| 6,836,278 B1 | 12/2004 | Saito et al. | |
| 6,997,923 B1 | 2/2006 | Anderson et al. | |
| 2001/0035999 A1 * | 11/2001 | Saito et al. | 359/204 |
| 2001/0053907 A1 * | 12/2001 | Ota | 606/10 |
| 2002/0002367 A1 | 1/2002 | Tankovich et al. | |
| 2002/0138072 A1 | 9/2002 | Black et al. | |
| 2002/0161357 A1 | 10/2002 | Anderson et al. | |
| 2003/0034959 A1 | 2/2003 | Davis et al. | |
| 2003/0045916 A1 * | 3/2003 | Anderson et al. | 607/89 |
| 2003/0109860 A1 | 6/2003 | Black | |
| 2003/0167033 A1 * | 9/2003 | Chen et al. | 604/20 |
| 2003/0216719 A1 * | 11/2003 | Debenedictis et al. | 606/10 |
| 2004/0000316 A1 | 1/2004 | Knowlton et al. | |
| 2004/0015157 A1 | 1/2004 | Connors et al. | |
| 2004/0143247 A1 | 7/2004 | Anderson et al. | |
| 2004/0152943 A1 | 8/2004 | Zimmerman et al. | |
| 2004/0189790 A1 * | 9/2004 | Yamakawa | 347/244 |
| 2005/0018199 A1 * | 1/2005 | LeBlanc | 356/477 |
| 2005/0137584 A1 * | 6/2005 | Lemchen | 606/1 |

FOREIGN PATENT DOCUMENTS

| | | |
|---|---|---|
| WO | WO 01/39834 A1 | 6/2001 |
| WO | WO 01/74265 | 10/2001 |
| WO | WO 04/86947 | 10/2001 |
| WO | WO 02/22035 | 3/2002 |

OTHER PUBLICATIONS

Andersen, Dan E. et al., "System for the automated photothermal treatment of cutaneous vascular lesions," *Journal of Biomedical Optics* 9(2) (Mar./Apr. 2004), pp. 308-314.

Apfelberg, David B. et al., "Dot or Pointillistic Method for Improvement in Results of Hypertrophic Scarring in the Argon Laser Treatment of Portwine Hemangiomas", *Lasers in Surgery and Medicine*, vol. 6 (1987), pp. 552-558.

Apfelberg, David B., "Intralesional Laser Photocoagulation—Sterioids as an Adjunct to Surgery for Massive Hermangiomas and Vascular Malformations," *Annals of Plastic Surgery*, vol. 35, No. 2 (Aug. 1995), pp. 144-149.

Fujii, Hitoshi et al., "Multispot laser photocoagulation system using a fiber bundle scanner," *Applied Optics*, vol. 21, No. 19, Oct. 1, 1982, pp. 3437-3442.

Guo, Ruixiang et al., "Application of an all-solid-state, frequency-doubled Nd:YAP laser to the generation of twin beams at 1080 nm," *Applied Optics*, vol. 41, No. 12, Apr. 20, 2002, pp. 2304-2307.

Manstein, Dieter et al., "Fractional Photothermolysis: A New Concept for Cutaneous Remodeling Using Microscopic Patterns of Thermal Injury," *Lasers in Surgery and Medicine*, vol. 34 (2004), pp. 426-438.

Mordon, Serge et al., "Using a 'Non Uniform Pulse Sequence' can Improve Selective Coagulation with a Nd;YAG Laser (1.06 micron) Thanks to Met-Hemoglobin Absorption: A Clinical Study on Blue Leg Veins," *Lasers in Surgery and Medicine*, vol. 32 (2003), pp. 160-170.

Ou, Z.Y. et al., "85% efficiency for cw frequency doubling from 1.08 to 0.54 microns," *Optics Letters*, vol. 17, No. 9, May 1, 1992, pp. 640-642.

Wyant, J.C., "Rotating Diffraction Grating Laser Beam Scanner," *Applied Optics*, vol. 14, May 1975, pp. 1057-1058.

Notification of Transmittal of the International Search Report and the Written Opinion, PCT/US04/43515, Nov. 15, 2005, 8 pages.

Fujii, H. et al., "Fibre bundle scanner for laser photocoagulation," *Optics and Laser Technology*, Feb. 1982, pp. 39-40.

Huzaira, Misbah et al., "Intradermal focusing of near-infrared optical pulses: A new approach for non-ablative laser therapy," *American Society for Laser Medicine and Surgery*, Supplement 15, 2003, Abstract 66, p. 21.

Khatri, K. et al., "Treatment of rhytids with subsurface-focused Er:YLF laser," *American Society for Laser Medicine and Surgery*, Supplement 15, 2003, Abstract 68, p. 21.

Manstein, D. et al., "Spatially Confined Photothermolysis of dermal targets using an IR-fiberlaser in combination with focusing and contact cooling," *American Society for Laser Medicine and Surgery*, Supplement 14, 2002, Abstract 92, p. 28.

Naess, Espen et al., "Computer-assisted laser photocoagulation of the retina—a hybrid tracking approach," *Journal of Biomedical Optics* 7(2), Apr. 2002, pp. 179-189.

* cited by examiner

US 7,090,670 B2

MULTI-SPOT LASER SURGICAL APPARATUS AND METHOD

BACKGROUND OF THE INVENTION

1. Field of the Invention

This invention relates generally to an array of light beams used to generate a pattern of spots, for example as can be employed in laser surgery and laser dermatology.

2. Description of the Related Art

In laser surgical applications, for example in laser dermatology, an optical system generates a light beam(s) of a desired size and energy and this light beam is used to treat a selected region of the patient's body (i.e., the treatment area). For example, in many dermatology applications, a hand piece is used to guide the laser beam to the treatment area. The hand piece is typically attached to one end of an articulated arm, which transmits the laser beam to the hand piece and also supports a wide range of motion for the hand piece.

A physician typically treats the treatment area by sweeping the laser hand piece back and forth over the treatment area. In many cases, the physician is guided by an aiming line, which may be generated by the hand piece. The sweeping may be either manual or automated. Automated sweeping can be achieved by mounting the laser or other light source on a movable carriage. Whatever the mechanism, as the laser beam is swept over the treatment area, the physician typically pulses the laser beam on and off, either manually or via automatic means, thereby regulating the exposure of the treatment area and creating a pattern of treatment spots over the treatment area.

Many laser technologies for dermatology use a single high power beam that is scanned across the treatment area to create a pattern of exposed areas or spots. In many cases, the spots overlap sufficiently that the entire treatment area is exposed. The treatment rates achievable by scanning a single beam in this manner can be sufficiently fast when a high power laser (typically>10 W) is used with a large diameter beam (typically 2–6 mm).

However, new treatments can use smaller spot sizes and more spots. For example, see co-pending U.S. patent applications Ser. No. 10/367,582, "Method and Apparatus for Treating Skin Using Patterns of Optical Energy," filed on Feb. 14, 2003; and Ser. No. 60/486,304, "Method and Apparatus for Fractional Phototherapy of Skin," filed Jul. 11, 2003; both of which are incorporated herein by reference. Traditional laser systems are not well suited for these applications because the laser beams generated by traditional systems typically are too large and too energetic. Traditional systems also are typically based on more expensive types of lasers and do not take advantage of lower power, cheaper semiconductor lasers. In addition, the single laser beam generated by traditional systems would have to be individually positioned to generate each of the spots in the overall pattern and, since there typically are a large number of spots in the pattern, the required scan time becomes unacceptably long.

Hence, there is a need for devices and methods that can generate a pattern of spots on a treatment area, preferably in an efficient manner.

SUMMARY OF THE INVENTION

The present invention overcomes the limitations of the prior art by providing a laser treatment apparatus in which an array of light beams is used to generate a treatment pattern of spots. In one approach, the array is swept along a main scan direction and dithered in a sub-scan direction to generate the pattern of spots. The array is elongated along the sub-scan direction and the dithering has a travel that is significantly less than the length of the array in the sub-scan direction.

The optical module that generates the array of light beams can take many different forms. For example, it can be based on a fiber coupled laser source diode, a laser source followed by beam splitting optics, a fiber laser source followed by a beam splitter, multiple light sources each of which generates one of the light beams in the array, or an external light source(s) for example coupled by an optical fiber. The light beams in the array can also be generated simultaneously, sequentially (e.g., by scanning a single light beam to multiple locations), or a combination of the two. The sub-scan module that dithers the array of light beams can also take many different forms. A movable carriage that can be translated in the sub-scan direction and a light deflecting module are two examples.

In one embodiment, multiple laser diodes are coupled into optical fibers. The terminating ends of the optical fibers are aligned into a 1×N array and imaged onto the treatment area to generate the spots. The total length of the array is approximately 1 cm. The array is dithered to form an irregular pattern of spots (e.g., see FIG. 3). The travel for the dithering is approximately equal to the spacing between light beams in the array. The dithering is accomplished by components in a hand piece; the hand piece is swept along the main scan direction. A main scan sensor tracks the velocity of the sweeping and a controller adjusts the dithering accordingly. The controller also controls the exposure of the light beams on the treatment area so that the spots are not over- or underexposed.

Other aspects of the invention include methods and systems corresponding to the apparatus described above, and applications for the above. One example application is medical treatments that use smaller spot sizes (for example, spots with diameters of 0.1 mm) and more spots (for example, spot densities of 2000 spots/cm$^2$) than conventional laser treatments. For example, see co-pending U.S. patent applications Ser. No. 10/367,582, "Method and Apparatus for Treating Skin Using Patterns of Optical Energy," filed on Feb. 14, 2003; and Ser. No. 60/486,304, "Method and Apparatus for Fractional Phototherapy of Skin," filed Jul. 11, 2003.

BRIEF DESCRIPTION OF THE DRAWINGS

These and other objects, features and advantages can be more readily understood from the following detailed description with reference to the accompanying drawings, wherein.

DETAILED DESCRIPTION OF THE PREFERRED EMBODIMENTS

Figure 1:
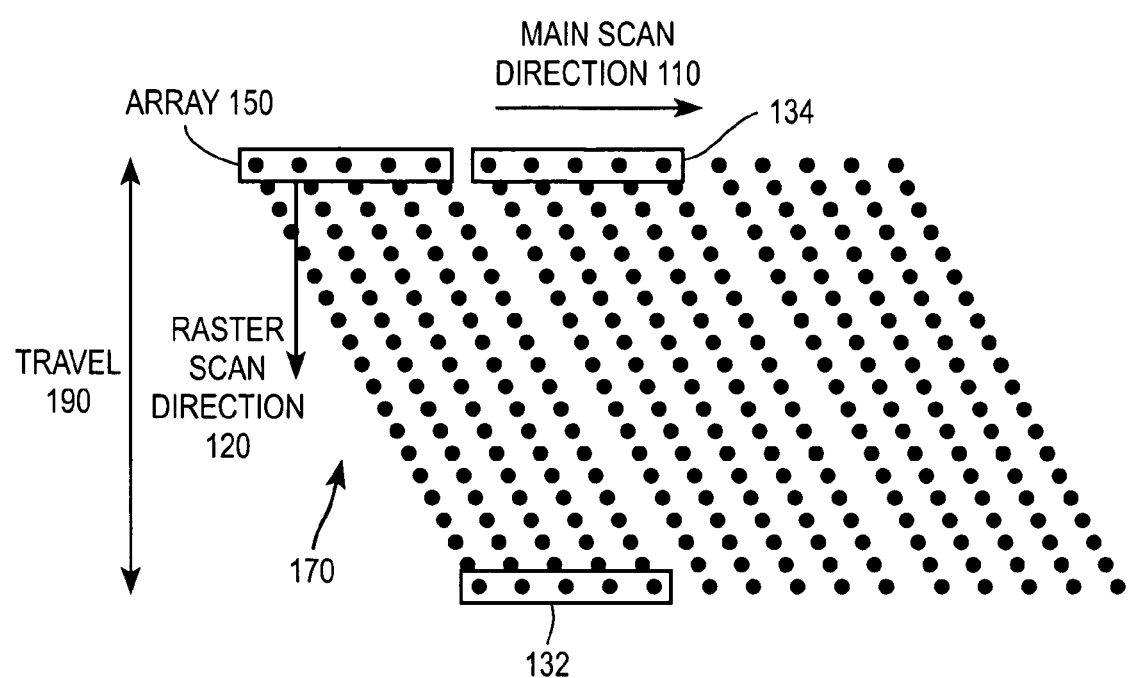
FIG. 1 is a diagram showing a pattern of spots generated by an array of light beams using a raster scan.

FIG. 1 shows a raster pattern for generating a pattern of spots. The row 150 of laser beams is aligned to the main scan direction 110 (i.e., the direction in which the physician sweeps the hand piece). While the array 150 is swept along the main scan direction 110, it is also raster scanned in the transverse direction 120. The laser beams are pulsed during this movement to produce the pattern of spots shown in FIG. 1. At the end 132 of each raster scan, the array is "reset" to the start position 134 of the next raster scan.

While this approach has many advantages compared to individually positioning a single laser beam to generate each of the spots in the pattern, one disadvantage of this approach is the travel 190 of the array 150 in the raster scan direction 120 can be long in certain applications. If the raster scan is accomplished by mechanically translating the light source, then the long travel increases the mechanical wear and tear and reduces the life of the system. The long travel can also make the hand piece bulky and reduce the speed or resolution of the overall scan. The raster scan pattern also leaves a tapered gap 170 at the start and end of the overall pattern. This type of raster scan also creates a regular pattern of spots. Artifacts of the regular pattern can be visible even when the individual spots are not, and this can be cosmetically undesirable.

Figure 2:
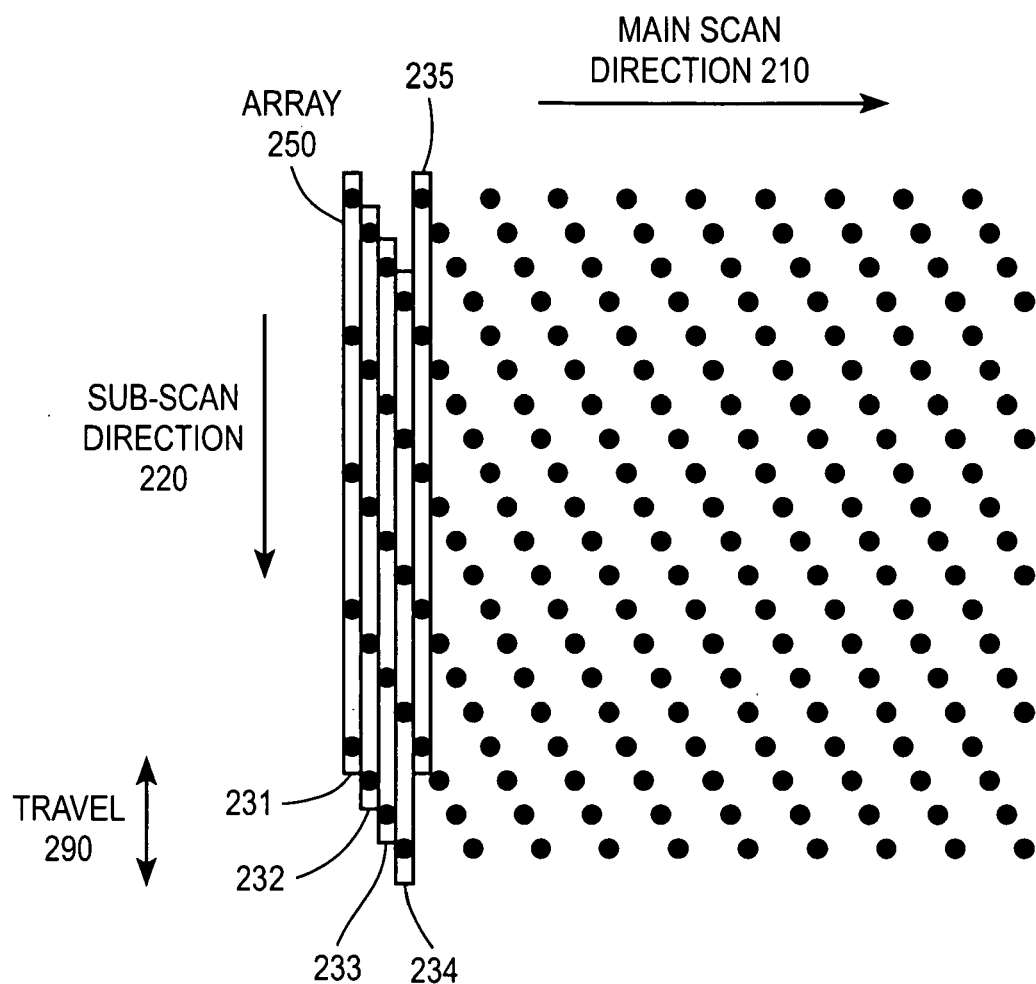
FIG. 2 is a diagram showing a pattern of spots generated by an array of light beams according to the invention.

FIG. 2 shows another approach for generating a treatment pattern. In this example, a 1×5 array 250 of light beams is aligned to be transverse to the main scan direction 210. As the array 250 is swept along the main scan direction 210, it is also dithered in the transverse sub-scan direction 220. In FIG. 2, the array is dithered to four different offsets in the sub-scan direction, beginning with 231 and ending with 234. It is then reset to the start position 235 for the next set of sub-scans. The total travel 290 in the sub-scan direction is significantly less than the length of the array in the sub-scan direction. In this example, the light beams (and resulting spots) are evenly spaced and the travel 290 in the sub-scan direction is approximately equal to the beam-to-beam spacing.

Figure 3:
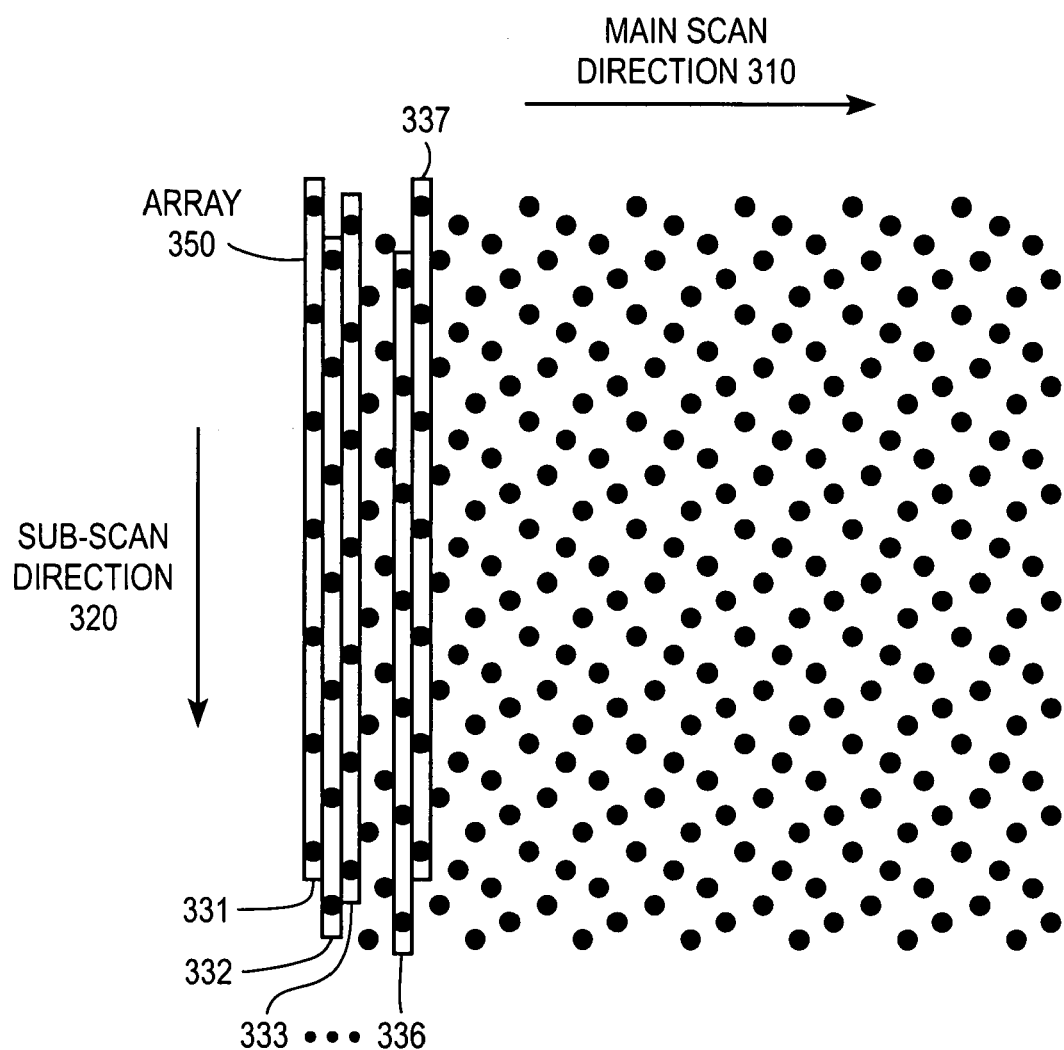
FIG. 3 is a diagram showing another pattern of spots generated by an array of light beams according to the invention.

FIG. 3 shows another treatment pattern generated according to the invention. This example uses a 1×7 array 350 of light beams. The array 350 is dithered in the sub-scan direction to six different locations, beginning with 331 and ending with 336, and then the sequence is repeated at 337. In FIG. 3, the offsets of locations 331-336 in the sub-scan direction are not a linear function of the main scan direction. In other words, the array 350 is not simply linearly scanned in the sub-scan direction. Rather, it jumps around to different locations as the main sweep progresses. The result is an irregular pattern of spots, as shown in FIG. 3, as compared to the regular pattern of FIG. 2.

One advantage of irregular patterns is that, compared to regular patterns, they are less likely to result in visible artifacts. In addition, an irregular pattern increases the distance between adjacent spot arrays. For example, the spots in arrays 331 and 332 are further separated than the spots in arrays 231 and 232. This increases the time between the generation of spots that are close to each other (e.g., arrays 331 and 333), thus allowing more cooling between exposures. Irregular patterns can also result in more uniform two-dimensional coverage. In FIG. 2, the resulting pattern is a set of parallel diagonal lines, where the spot coverage is densely grouped in the direction along the lines and sparsely grouped in the orthogonal direction. In FIG. 3, the spot density is more uniform over all directions.

FIGS. 2 and 3 are merely two examples of arrays and patterns. Other variations will be apparent. For example, both FIGS. 2 and 3 used a basic dither sequence (231-234 in FIG. 2, and 331-336 in FIG. 3) that was repeated. Non-periodic or random/quasi-random dither sequences can also be used.

As another example, the array of light beams can take different shapes. The examples in FIGS. 2 and 3 can be straightforwardly extended from 1×N arrays of light beams to a rectangular m×n array of light beams, where there would be n rows of m light beams each and the travel in the sub-scan direction would be approximately equal to (or less than) the row-to-row spacing. The examples in FIGS. 2 and 3 can be considered to be an array of n rows with 1 light beam in each row. The array can also be non-rectangular in shape. It can be based on a grid with non-orthogonal coordinates (e.g., a hexagonal grid) or not even be grid-based at all. For example, the array could contain a number of light beams that were irregularly or non-uniformly distributed, so long as the resulting array was elongated in the sub-scan direction.

As used in this application, the term spot is meant to refer to a treatment location within a treatment area, for example a region on the patient's skin in a dermatological application, to which a light beam is directed in order to treat that location. The exposure of the light beam on the location typically can be varied in duration and/or intensity and the resulting exposure creates the spot within the treatment area. After a spot is created, the light beam typically is moved to a different location to create another spot. In this way, successive movement of the light beams over many locations results in treatment of the treatment area. The end result is a two-dimensional pattern of spots or, in some cases, a three-dimensional pattern depending on how deep the optical energy penetrates.

Figure 4:
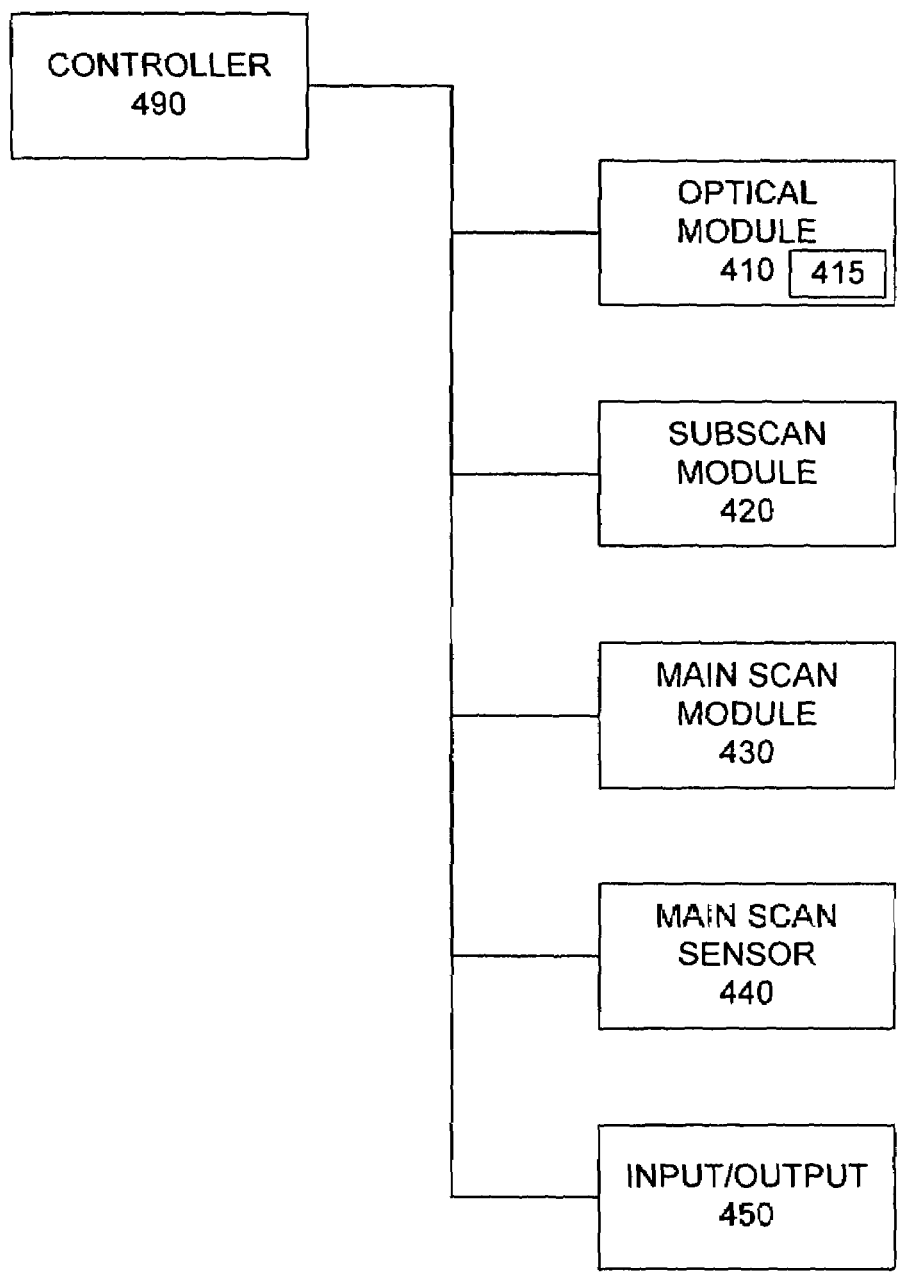
FIG. 4 is a block diagram of a light treatment apparatus for generating an array of light beams according to the invention.

FIG. 4 is a block diagram of a light treatment apparatus for generating an array of light beams according to the invention. The apparatus includes an optical module 410, either with or without an optical source 415, and a sub-scan module 420. The apparatus optionally also includes a main scan module 430, a main scan sensor 440 and/or input/output 450. A controller 490 is coupled to the different components as applicable.

The apparatus operates as follows. The optical module 410 generates the array of light beams that is used to form the pattern of spots. The sub-scan module 420 is coupled to the optical module 410 and dithers the array of light beams in the sub-scan direction, as described above. The main scan module 430 is also coupled to the optical module 410 and sweeps the array of light beams along the main scan direction. If the apparatus does not do the sweeping (e.g., if the physician manually sweeps the array), then there is no need for a main scan module 430. The main scan sensor 440, if present, senses motion of the array of light beams along the main scan direction and this information can be used different purposes, as described below. The input/output 450 is conventional. Examples include a touch screen, keypad, liquid crystal display, electrical connector, wireless connection, etc.

Referring to each of the components in more detail, the optical module 410, which generates the array of light beams, can be implemented in a number of different ways. If the optical module 410 includes an optical source 415, then the array of light beams can be generated from the output of the optical source 415. Alternately, the optical module 410 may not have its own optical source 415. Rather, the optical module 410 could include an optical input port (e.g., an optical fiber) that receives an input light beam(s) from an external source. Optics within the optical module 410 then generate the outgoing array of light beams from the input light beam(s).

In addition, the light beams in the array can be generated simultaneously. For example, a single light beam can be optically split into multiple beams, all of which are simultaneously on or off. Examples of optical splitters include fiber optic splitters, integrated waveguide splitters, gratings, diffractive elements, multi-faceted optical components (i.e., with different regions, each of which is illuminated and directs a portion of the light beam to a different location) and free space beamsplitters.

Alternately, the light beams can be generated sequentially in time. For example, a light deflecting module can deflect a light beam to the first position in the array, then to the second position, then to the third, etc. Examples of light deflectors include scan mirrors (i.e., galvanometers), acousto-optic devices, and rotating optical elements (e.g., with facets that are sequentially illuminated as each facet rotates through the optical beam). The two approaches can also be combined. For example, three light beams may be sequentially deflected to each of four different positions to create an array with twelve light beams.

The array of light beams can also be generated from multiple sources. Each source can be used to generate one of the light beams in the array. For example, an array of laser diodes can be imaged onto the treatment area to form the array of light beams. In fact, multiple sources can even be combined to form each of the light beams in the array. In one approach, different sources are coupled into the optical module 410 by fiber bundles, with at least three fibers of uniform size in a bundle. Each fiber bundle generates one of the light beams in the array.

The wavelengths of the light beams depend in part upon the application (e.g., the type of dermatological condition to be treated). Lasers having different wavelengths are used in surgical applications such as dermatology. Examples of laser light sources include diode lasers, diode-pumped solid state lasers, Er:YAG lasers, Nd:YAG lasers, argon-ion lasers, He—Ne lasers, carbon dioxide lasers, excimer lasers, erbium fiber lasers, and ruby lasers. These devices generate laser beams having the wavelength in the visible range of the spectrum (0.4 –0.7 µm) as well as in infrared (0.7–11 µm) and UV (0.18 –0.40 µm) ranges. It should be noted that terms such as "optical" and "light" are meant to include all of these wavelength regions and not just the visible range of the spectrum. Candela Laser Corp. of Wayland, Mass., Coherent, Inc. of Santa Clara, Calif. and other manufacturers market these types of lasers.

The optical source could include one particular type of laser light source capable of providing one wavelength or a wavelength range. Alternatively, the optical source could include two or more different types of laser light sources to provide a variety of different wavelengths or wavelength ranges. Light beams from different laser light sources can be directed to the treatment area either simultaneously or sequentially. For example, see co-pending U.S. patent application Ser. No. 10/017,287, "Multiple Laser Treatment," filed on Dec. 12, 2001 and incorporated by reference herein.

For certain embodiments, the optical source is desirably a diode laser, such as an infrared diode laser. For other embodiments, the optical source is desirably a fiber laser, such as an erbium fiber laser manufactured by IPG Photonics of Oxford, Mass. However, while lasers are the preferred embodiment of the optical source described here, other optical sources such as a flashlamp can also be used.

Referring now to the sub-scan module 420, the optical module 410 generates the array of light beams and the sub-scan module 420 dithers the array in the sub-scan direction. These two modules are shown as separate in FIG. 4, but this is purely for illustrative purposes. In actual implementations, the two modules may be separate, or they may be integrated together. In an example where the two are separate, the optical module 410 can be upstream of the sub-scan module 420 in the optical train. The optical module 410 generates the array of light beams; the sub-scan module 420 receives the array and then dithers the array of light beams. Alternatively, the sub-scan module 420 can be upstream of the optical module 410. For example, the sub-scan module 420 can dither an incoming light beam; the optical module 410 receives the dithered light beam and splits it into the array of light beams. The two modules can also be integrated together. For example, if a single galvanometer with a diffractive grating for the reflective element is used to both generate the array of light beams by diffraction, and also to implement the dither function, then the two modules effectively are implemented as a single unit. For convenience, the two modules are described as being "coupled" to each other. This is intended to be interpreted broadly, including all of the configurations described above. Similar remarks apply to other components that are "coupled" to each other.

The sub-scan module 420 can be implemented in a number of different ways. Conventional techniques for dithering a light beam or an array of light beams can be used. For example, the optical source generating the array or other components within the optical train can be physically moved, for example by mounting the components on a slide or a movable carriage. Alternately, the light beams can be dithered by optically deflecting the beams. Scan mirrors (i.e., galvanometers), acousto-optic devices, and rotating optical elements are some examples.

The optional main scan module 430 sweeps the array of light beams along the main scan direction. The underlying function (steering light beams) is similar to that of the sub-scan module 420, although the total travel and desired speed may be significantly different. Thus, the same conventional approaches are also candidates for the main scan module, although the actual implementation may be significantly different due to the travel and speed considerations. For example, both sweeping and dithering may be implemented by physical translation. But the main scan module 430 may sweep across several inches or feet at a moderate speed; whereas the sub-scan module 420 dithers across a fraction of an inch at much higher speeds. Thus, the main scan module 430 may be implemented by a robotic arm that holds the hand piece of the apparatus; whereas the sub-scan module 420 may be implemented by a small carriage mounted on rails, located internal to the hand piece.

The main scan sensor 440 senses the sweeping motion and can be implemented in different ways. For example, the main scan sensor 440 can measure relative position or velocity, similar to the mechanisms used in certain types of computer mouse. Alternately, it can measure absolute position, using triangulation from known beacons, or GPS or similar systems.

The information gathered by the main scan sensor 440 can be used for different purposes. The information can be used as feedback to control automated sweeping by the main scan module 430, or can also be used to control or coordinate the dithering by the sub-scan module 420. For example, if the physician's sweeps at an uneven speed,then the dithering speed can be automatically adjusted to match the physician'sweep speed. For example, see co-pending U.S. patent application Ser. No. 10/745,761, "Method And Apparatus For Monitoring and Controlling Laser-Induced Tissue Treatment," filed on Dec. 23, 2003 and incorporated by reference herein.

The controller 490 may be used to control the placement, intensity, duration and other characteristics of the light beams in order to generate the spots on the treatment area. The controller 490 can be implemented in many different forms: for example, electromechanical systems, dedicated electronic circuitry, ASIC, microprocessor, programmable DSPs, software, or combinations of the above. The controller 490 communicates with the different components 410–450, as applicable. In general, a controller may respond to preprogramming or operator activation (e.g., via the input/output 450).

Control parameters can be used to specify the location of each spot in the pattern; the dither amounts and/or dither sequence for the array of light beams in the sub-scan direction; when to line feed in the main scan direction (i.e., reset to the beginning of the next sweep); the intensity of the light beams to be generated; the duration of the illumination; and/or when to turn on or off a particular light beam in the array (individual beams can be turned on and off independently in some embodiments). Thus, the control parameters can be used to specify the amount of exposure commensurate with a treatment goal. The control parameters can be hard wired. Alternately, an operator may program the control parameters, for example via the input/output 450. In an embodiment, these control parameters are stored in the memory.

For purposes of non-ablative coagulation of a dermal layer of the treatment area, a laser light source can provide an optical beam having a wavelength of approximately 1.5 μm and an optical fluence incident on the outer surface of the skin between approximately 0.1 Joules/cm$^2$ and 100,000 Joules/cm$^2$, such as between approximately 1 Joules/cm$^2$ and 1000 Joules/cm$^2$. For certain applications, the pulse duration of an optical beam can be approximately equal to or less than a thermal diffusion time constant, which is approximately proportional to the square of the diameter of the focal spot within the treatment area. Pulse durations that are longer than the thermal diffusion time constant can be less efficient and cause the spot to undesirably grow or shrink by thermal diffusion. It should be noted that the light beams might accomplish the goal of completely treating the treatment area in one pass or in multiple passes.

Figure 5:
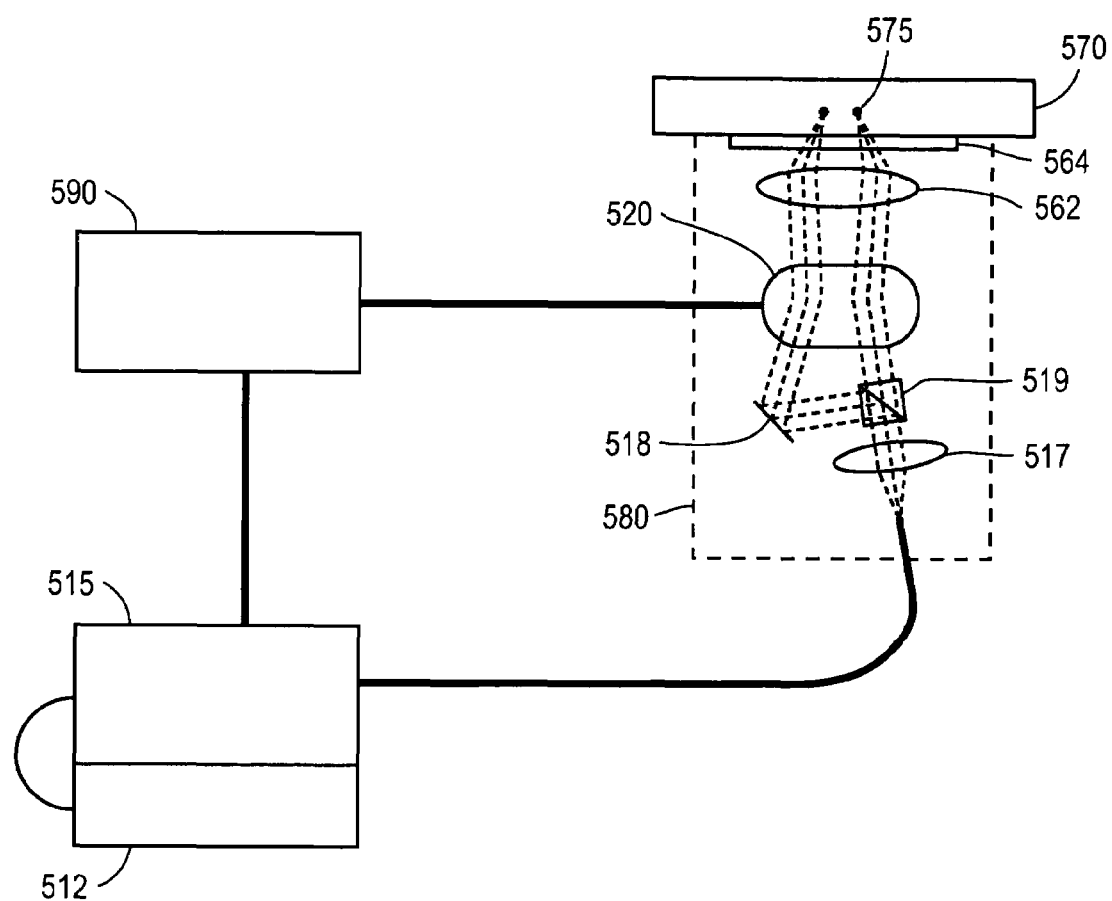
FIG. 5 is a diagram of one implementation of a light treatment apparatus using a single light source.

FIG. 5 is a diagram of one implementation of a light treatment apparatus using a single light source. In this example, the optical source is based on an Erbium fiber laser 515, which has a wavelength of 1.54 μm. The laser 515 is driven by a pulse source 512. The controller 590 adjusts the timing and duration of the pulses to control the exposure of the spots 575 in the treatment area 570. The light beam from the fiber laser 515 is delivered through a single-mode fiber 516 to the hand piece 580. A collimating lens 517 collimates the output from the single-mode fiber 516. A beamsplitter 519 divides the collimated beam into two collimated beams of roughly equal power. In alternate embodiments, additional optics can be used to generate additional beams. A focusing lens 562 focuses each collimated beam to a spot 575 within the skin 570. A flat sapphire plate 564 is in contact with the skin. It serves as an optical window for the hand piece 580 and also allows the light beams to be focused to the same depth within the skin for each of the beams. In this example, the array of light beams is a 1×N array and is about 1 cm long in the sub-scan direction. The window 564 is slightly larger. The optical components preferably are anti-reflection coated to maximize the optical power that is coupled into the skin.

Additional optics 520 between the collimating and focusing elements 517 and 562 dither the location of the multiple light beams on the surface of the skin. In this implementation, optical elements 520 are rotated by motors in the hand piece. Each optical element is divided into different facets, each of which dithers the light beams by different amounts. When the elements are rotated, the array of light beams is sequentially dithered to the different locations, thus generating the pattern of spots. For example, see co-pending U.S. patent application Ser. No. 10/750,790, "High Speed, High Efficiency Optical Pattern Generator using Rotating Optical Elements," filed on even date herewith and incorporated by reference herein.

The user can adjust the distance between adjacent spots in the treatment pattern according to the desired treatment level. In addition, selected spots within the pattern can be turned off if a larger range of treatment levels is desired. A velocity sensor in the tip of the hand piece measures the speed of the hand piece as it moves across the treatment area. If the user changes the velocity of the hand piece across the skin, the controller 590 adjusts the rate at which the apparatus generates spots.

Figure 6:
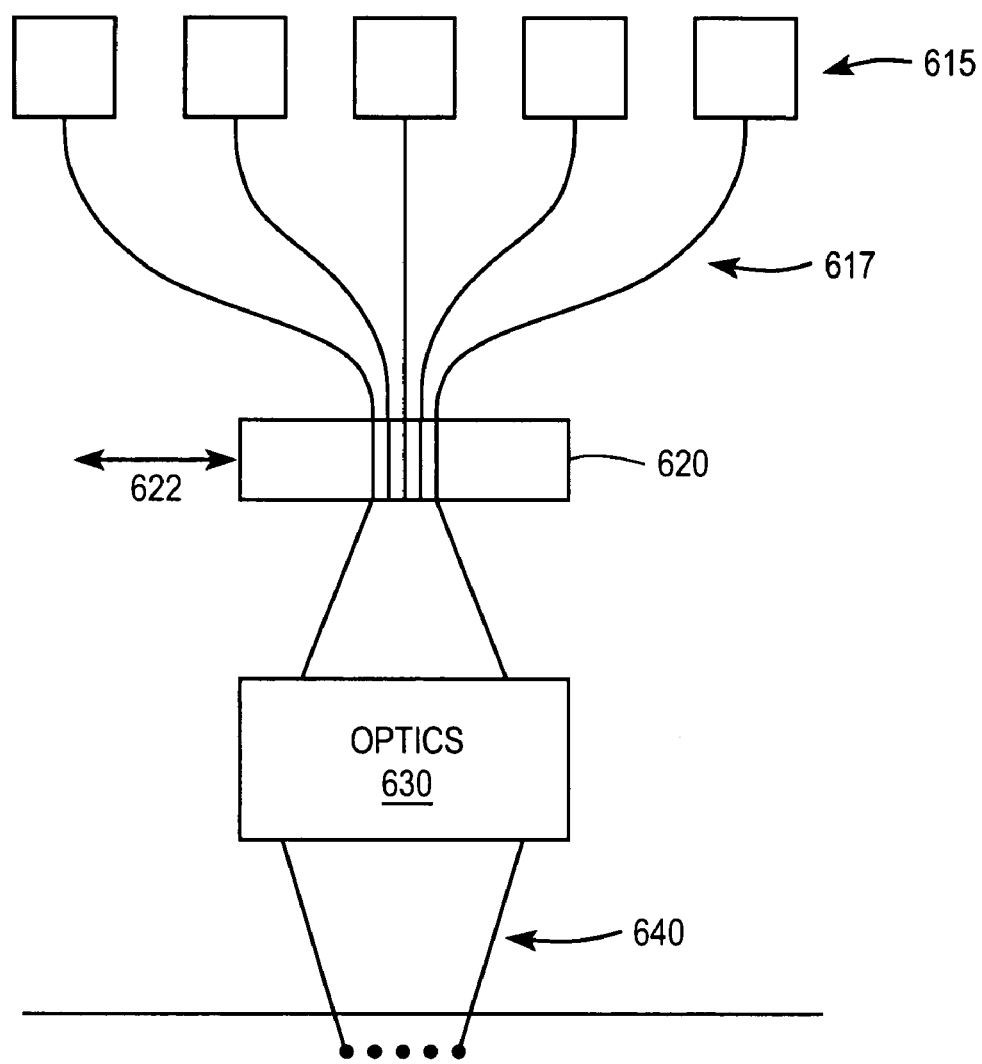
FIG. 6 is a diagram of another implementation of a light treatment apparatus using multiple light sources.

FIG. 6 is a diagram of another implementation of a light treatment apparatus using multiple light sources. In this example, five diode lasers 615 are coupled into high brightness glass fiber pigtails 617. The pigtails are arranged to form a 1×N array (N=5). Each of the diode lasers 615 provides 1 W of continuous or pulsed power. Higher or lower power optical sources can be used. Some industrial systems can be purchased with a thermoelectric cooler, heat sink, fan, power supply and component electronics all in one package. The fibers 617 are terminated with an epoxy-free industry standard connector for high power lasers to which an optional commercially available collimating lens adapter 630 can be attached and passively aligned. This arrangement can be used to produce an array 640 of closely spaced light beams of about the same size and intensity. Customized optics and/or housings can be used to achieve a closer spacing. The fiber pigtails are mounted on a carriage 620 that is moveable in the sub-scan direction 622. A motor drives the carriage, thus dithering the array of light beams in the sub-scan direction.

Although specific embodiments of the invention have been described with reference to the drawings, it should be understood that the embodiments shown are by way of examples only and merely illustrative of but few of many possible specific embodiments, which represent application of the principles of the invention. For example, there is no need for a mechanical device or a carriage to sweep the laser beam over a treatment area in the main scan direction. This can be accomplished using a manual method, such as a hand piece that a physician or other operator moves over a treatment area. As another example, the transverse sub-scan direction can make angles other than 90 degrees with respect to the main scan direction. For example, for spots placed on a hexagonal grid pattern, the transverse sub-scan direction may be at 60 degrees to the main scan direction. Another common angle that can be used is 75 degrees. Various changes and modifications obvious to one skilled in the art to which the invention pertains are deemed to be within the spirit, scope and contemplation of the invention as further defined in the appended claims. Furthermore, no element, component or method step is intended to be dedicated to the public regardless of whether the element, component or method step is explicitly recited in the claims.

What is claimed is:

1. A light treatment apparatus for generating a pattern of spots over a treatment area, comprising:
   an optical module for generating an array of light beams, wherein the array is elongated along a sub-scan direction that is transverse to a main scan direction;
   a sub-scan module coupled to the optical module for dithering the array of light beams in the sub-scan direction; wherein, for a sweep of the array along the main scan direction, a travel of the array in the sub-scan direction is not more than the length of the array in the sub-scan direction;
   a main scan sensor for sensing sweeping of the array along the main scan direction; and
   a controller coupled to the sub-scan module and the main scan sensor, for controlling dithering of the array in response to the sensed sweeping of the array along the main scan direction.

2. The apparatus of claim 1 wherein the optical module comprises:
   a fiber coupled laser diode.

3. The apparatus of claim 1 wherein the optical module comprises:
   a fiber laser.

4. The apparatus of claim 1 wherein the optical module comprises:
   a laser for generating a laser beam; and
   optics coupled to the laser for generating the array of light beams from the laser beam.

5. The apparatus of claim 1 wherein the optical module comprises:
   a plurality of light sources; and optics coupled to the light sources for generating the array of light beams from the plurality of light sources.

6. The apparatus of claim 1 wherein the optical module comprises:
   an optical input port for receiving one or more input light beams from an external source; and
   optics coupled to the optical input port for generating the array of light beams from the received input light beams.

7. The apparatus of claim 6 wherein the optical input port comprises an optical fiber.

8. The apparatus of claim 1 wherein the optical module generates all of the light beams simultaneously.

9. The apparatus of claim 1 wherein the optical module generates the light beams sequentially in time.

10. The apparatus of claim 1 wherein the sub-scan module comprises:
    a movable carriage that can be translated in the sub-scan direction.

11. The apparatus of claim 1 wherein the sub-scan module comprises:
    a light deflecting module configured to deflect one or more of the light beams.

12. The apparatus of claim 1 wherein the array of light beams is a rectangular array of light beams with N rows in the sub-scan direction, and N is an integer greater than 1.

13. The apparatus of claim 12 wherein N>2.

14. The apparatus of claim 13 wherein the travel in the sub-scan direction is not more than a row-to-row spacing in the sub-scan direction.

15. The apparatus of claim 1 wherein the array of light beams is a 1×N array of light beams, and N is an integer greater than 1.

16. The apparatus of claim 1 wherein the array of light beams has a total array length of about 1 cm in the sub-scan direction.

17. The apparatus of claim 1 wherein the sub-scan direction is perpendicular to the main scan direction.

18. The apparatus of claim 1 wherein the travel of the array in the sub-scan direction is less than one half of the length of the array in the sub-scan direction.

19. The apparatus of claim 1 further comprising:
    a main scan module coupled to the optical module for automatically sweeping the array of light beams along the main scan direction.

20. The apparatus of claim 1 wherein the controller adjusts a location and/or an exposure of the light beams to generate the pattern of spots.

21. The apparatus of claim 20 wherein the pattern of spots produces fractional phototherapy of the treatment area.

22. The apparatus of claim 20 wherein the pattern of spots is an irregular pattern of spots.

23. A method for generating a pattern of spots over a treatment area, comprising:
    generating an array of light beams, wherein the array is elongated along a sub-scan direction;
    sweeping the array of light beams along a main scan direction that is transverse to the sub-scan direction; and
    for a sweep of the array along the main scan direction, automatically dithering the array in. the sub-scan direction, wherein a travel of the array in the sub-scan direction is not more than a length of the array in the sub-scan direction and the sweeping along the main scan direction and the dithering in the sub-scan direction generate the pattern of spot, and the step of automatically dithering the array of light beams in the sub-scan direction comprises:
    sensing sweeping of the array along the main scan direction; and
    controlling dithering of the array in response to the sensed sweeping of the array along the main scan direction.

24. The method of claim 23 wherein the step of generating an array of light beams comprises:
    generating all of the light beams simultaneously.

25. The method of claim 23 wherein the step of generating an array of light beams comprises:
    generating the light beams sequentially in time.

26. The method of claim 23 wherein the array of light beams is a rectangular array of light beams with N rows in the sub-scan direction, and N is an integer greater than 1.

27. The method of claim 26 wherein the travel in the sub-scan direction is not more than a row-to-row spacing in the sub-scan direction.

28. The method of claim 23 wherein the step of sweeping the array of light beams along a main scan direction comprises:
    automatically sweeping the array of light beams along the main scan direction.

29. The method of claim 23 wherein the step of sweeping the array of light beams along a main scan direction comprises:
    manually sweeping the array of light beams along the main scan direction.

30. The method of claim 23 further comprising:
    adjusting an exposure of the light beams in the array.

31. The method of claim 23 wherein the pattern of spots produces fractional phototherapy of the treatment area.

32. The method of claim 23 wherein the pattern of spots is an irregular pattern of spots.

33. The method of claim 23 wherein the step of controlling dithering of the array comprises:
controlling a placement of the light beams in the sub-scan direction in response to the sensed sweeping of the array along the main scan direction.

34. The method of claim 23 wherein the step of controlling dithering of the array comprises:
controlling an intensity of the light beams in response to the sensed sweeping of the array along the main scan direction.

35. The method of claim 23 wherein the step of controlling dithering of the array comprises:
controlling a duration of the light beams in response to the sensed sweeping of the array along the main scan direction.

36. The method of claim 25 wherein the step of controlling dithering of the array comprises:
controlling turning the light beams on or off in response to the sensed sweeping of the array along the main scan direction.

* * * * *

UNITED STATES PATENT AND TRADEMARK OFFICE
CERTIFICATE OF CORRECTION

PATENT NO. : 7,090,670 B2 Page 1 of 1
APPLICATION NO. : 10/751041
DATED : August 15, 2006
INVENTOR(S) : Robert Kehl Sink It is certified that error appears in the above-identified patent and that said Letters Patent is hereby corrected as shown below:

Column 10,
Line 28, delete the period after "in".

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,090,670 B2  Page 1 of 1
APPLICATION NO. : 10/751041
DATED : August 15, 2006
INVENTOR(S) : Robert Kehl Sink It is certified that error appears in the above-identified patent and that said Letters Patent is hereby corrected as shown below:

Column 12,
Line 6, replace "claim 25" with --claim 23--.

Signed and Sealed this

Fifteenth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,090,670 B2  Page 1 of 1
APPLICATION NO. : 10/751041
DATED : August 15, 2006
INVENTOR(S) : Robert Kehl Sink It is certified that error appears in the above-identified patent and that said Letters Patent is hereby corrected as shown below:

Column 10, line 33, delete "spot" insert --spots--.

Signed and Sealed this

Thirty-first Day of March, 2009

JOHN DOLL
*Acting Director of the United States Patent and Trademark Office*